(12) United States Patent
Pedrazzini

(10) Patent No.: US 8,678,738 B2
(45) Date of Patent: Mar. 25, 2014

(54) EQUIPMENT FOR TRANSFERRING BIOLOGICAL PRODUCT CONTAINERS WITH ADJUSTABLE INCLINATION OF ITS TRANSLATION AXIS

(75) Inventor: Gianandrea Pedrazzini, Paradiso (CH)

(73) Assignee: Inpeco Holding Ltd, Valletta VLT (MT)

( * ) Notice: Subject to any disclaimer, the term of this patent is extended or adjusted under 35 U.S.C. 154(b) by 0 days.

(21) Appl. No.: 13/697,616

(22) PCT Filed: May 5, 2011

(86) PCT No.: PCT/EP2011/057198
§ 371 (c)(1),
(2), (4) Date: Nov. 13, 2012

(87) PCT Pub. No.: WO2011/141348
PCT Pub. Date: Nov. 17, 2011

(65) Prior Publication Data
US 2013/0058752 A1    Mar. 7, 2013

(30) Foreign Application Priority Data
May 13, 2010   (IT) .............................. MI2010A0852

(51) Int. Cl.
*B65G 47/90*   (2006.01)
(52) U.S. Cl.
USPC ............ 414/751.1; 212/73; 212/75; 414/590; 414/728
(58) Field of Classification Search
USPC ......... 414/226.05, 590, 591, 626, 738, 751.1, 414/917
See application file for complete search history.

(56) References Cited

U.S. PATENT DOCUMENTS

| 4,449,884 A | * | 5/1984 | Motoda ...................... 414/751.1 |
| 5,825,105 A | * | 10/1998 | Barber et al. .............. 310/12.31 |
| 6,223,413 B1 | * | 5/2001 | Crocker et al. .............. 29/524.1 |

FOREIGN PATENT DOCUMENTS

| DE | 3718851 | | 2/1988 | |
| DE | 3718851 A1 | * | 2/1988 | ................ B65B 5/10 |
| GB | 725662 | | 3/1955 | |
| WO | 2004/070391 | | 8/2004 | |
| WO | 2009/068574 | | 6/2009 | |

* cited by examiner

Primary Examiner — Saul Rodriguez
Assistant Examiner — Brendan Tighe
(74) Attorney, Agent, or Firm — Jacobson Holman PLLC

(57) ABSTRACT

Equipment for transferring biological products containers from an interface support to a transport device and vice-versa for biological containers, positioned at different heights. The equipment including a frame to which a holding device for biological products containers is connected vertically mobile with respect to the frame and provided with fingers suitable to hold, transfer and release a container for biological products. The frame is integer with a sliding device along a bar fixed to an inclinable body. The inclinable body being in its turn rotatingly connected to a sustaining body, and a regulation device for the inclination of the inclinable body, and consequently of the bar, with respect to the sustaining body being present in function of the difference of height existing between the interfacing support and the transport device for biological products containers.

5 Claims, 7 Drawing Sheets

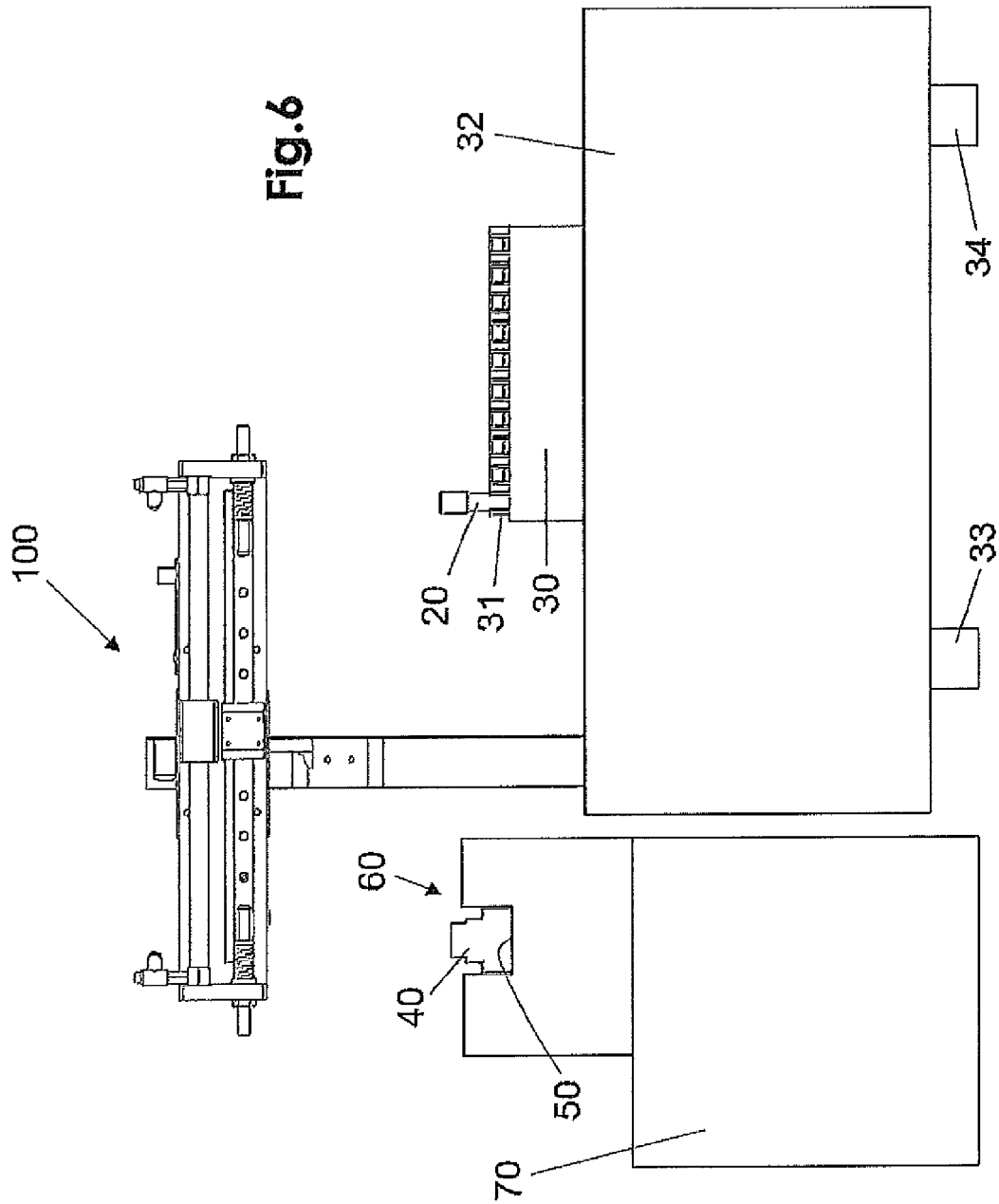

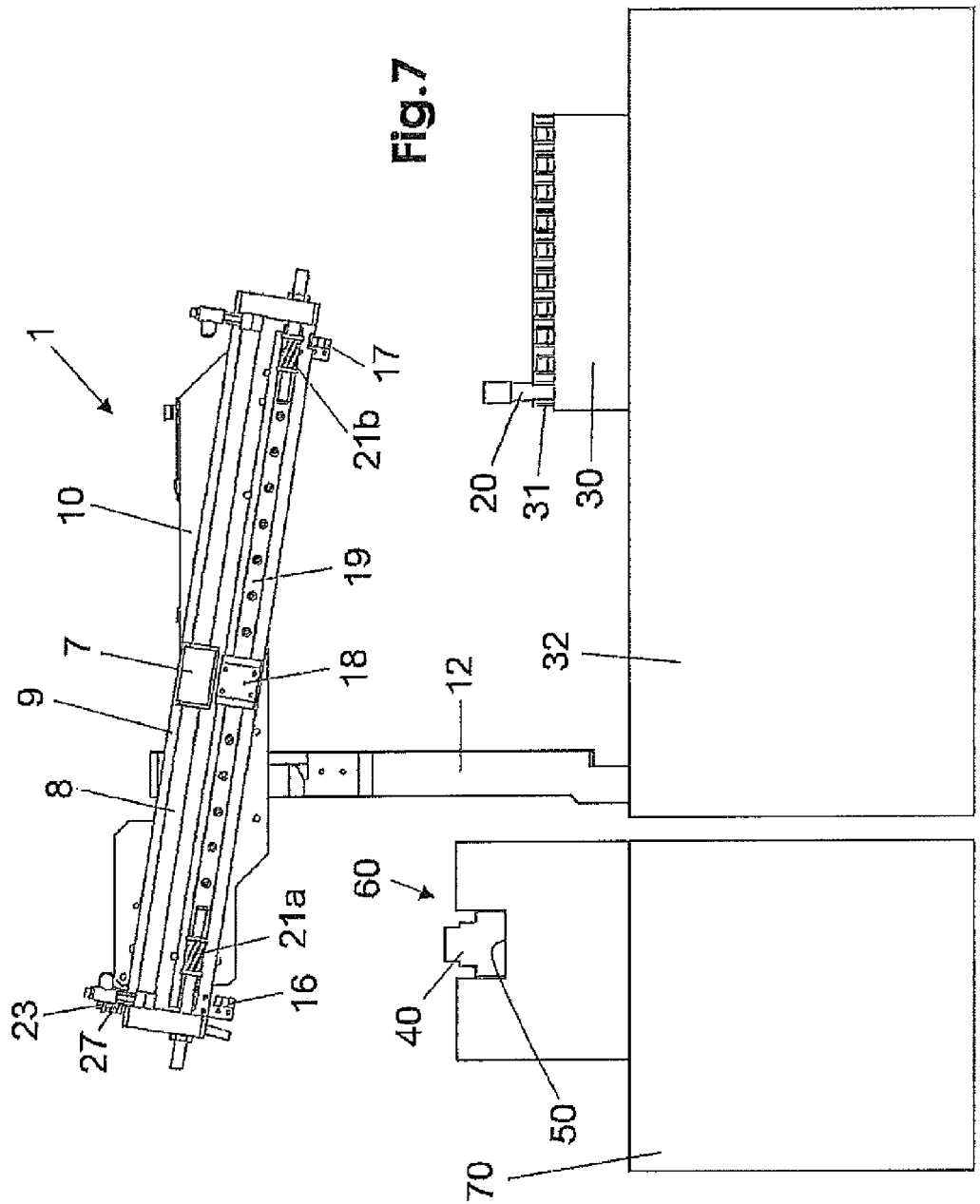

EQUIPMENT FOR TRANSFERRING BIOLOGICAL PRODUCT CONTAINERS WITH ADJUSTABLE INCLINATION OF ITS TRANSLATION AXIS

This is a national stage of PCT/EP11/057,198 filed May 5, 2011 and published in English, which has a priority of Italian no. MI2010A000852 filed May 13, 2010, hereby incorporated by reference.

The present invention relates to an equipment for transferring biological products containers with adjustable inclination translation axis.

Nowadays, in automated diagnostics and research laboratories in which various type of analyses are carried out on specimens of biological material preserved in containers, the need to transfer said containers between an automation system (e.g. the one described in application PCT No. PCT/EP2008/066220 by the same Applicant) and analysis or processing modules is increasingly felt.

The known equipment for transferring biological products containers comprises a fixed frame to which a holding device of such containers is connected, which holding device moves along the vertical from an upper to a lower position, as previously described in European Patent No. 1595148 by the Applicant.

In particular, once the frame is positioned exactly on the vertical with respect to the container to be picked, the holding device moves down to the lower position to pick the container by means of mobile gripping fingers from an interfacing support, positioned for example on an analysis or processing module; it then moves up and once the frame is positioned exactly on the vertical with respect to a transport device of such containers positioned on the automation system it is moved down again to the lower position, releasing the container into the transport device.

Obviously, the opposite operation is possible, i.e. the transfer of the biological products container from the transport device to the interfacing support.

Consequently, the movement of the entire equipment is obtained along three reciprocally orthogonal directions: the fixed frame moves along the two directions orthogonal to a hypothetical surface parallel to a horizontal reference surface to be alternatively positioned at the interfacing support and the transport device; subsequently, when the desired position is reached, the holding device moves down along the vertical direction, orthogonal in turn to said hypothetical surface.

The stroke of the holding device along the vertical axis is fixed, and thus the interfacing support and the transport device must be at the same height for using this equipment.

Problems occur when, due to the particular arrangement of the machinery in the analysis laboratory or simply due to the construction features or size of the same, there is a difference in height between the positions of the interfacing support and of the transport device of the biological products containers.

Indeed, in this case, the picking and releasing heights of the containers are different from one another and the known equipment cannot transfer as desired, because, as mentioned, in order to be alternatively positioned at the interfacing support and the transport device said frame only moves along the hypothetical flat surface to then move down again by the same height to either pick or release the container by means of the fixed stroke holding device.

It is thus necessary to raise the lower of the two machines between which the transfer occurs, for example by applying feet to the base of the same so as to align the height of the interfacing support and the transfer device, and thus allow the equipment to correctly transfer the biological products containers.

Such a solution is however particularly inconvenient because feet are needed for each pair of machines between which transfer occurs, which feet have in the various cases a specific height allowing to align the height of the interfacing support and of the transport device; furthermore the presence of such feet at the base of machines of often large size would make the resting of the machine itself on the ground not very stable.

It is an object of the present invention to make an equipment for transferring biological products containers capable of overcoming the problems illustrated above, ensuring an adequate transfer of the same from the interfacing support to the transport device, and vice-versa, if they are at different heights, without modifying neither the fixed stroke along the vertical axis of the holding device nor the height with respect to the ground of the machines between which transfer occurs and which accommodate the interfacing support or the transfer device.

These and other objects are reached by equipment for transferring biological products containers from an interfacing support to a transport device for biological containers and vice-versa, positioned at different heights, comprising a frame to which a holding device for biological products containers is connected vertically mobile with respect to said frame and provided with fingers suitable to hold, transfer and release a container for biological products, characterized in that said frame is integer with sliding means along a bar fixed to an inclinable body, said inclinable body being in its turn rotatingly connected to a sustaining body, and regulation means for the inclination of said inclinable body, and consequently of said bar, with respect to said sustaining body being present in function of the difference of height existing between said interfacing support and said transport support for biological products containers.

These and other features of the present invention will be further apparent from the following detailed description of an example of embodiment thereof, shown by way of non-limitative example in the accompanying drawings, in which.

Figure 1:
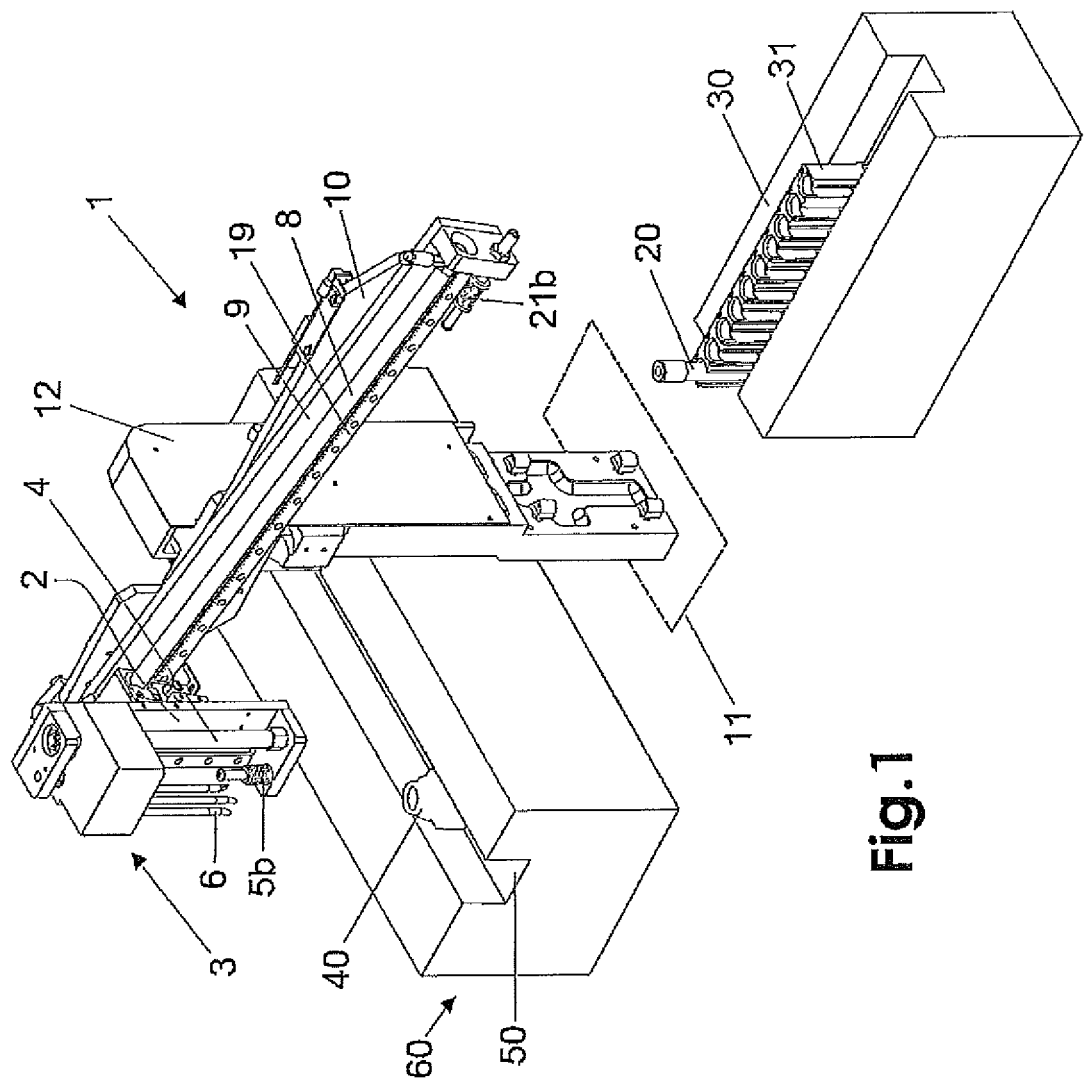
FIG. 1 is a perspective view of the equipment according to the invention at a step of resting.

FIGS. 6 and 7 both show front views of two different configurations of machines involved in the transfer of biological products containers referred respectively to the use of known equipment and equipment according to the invention.

Equipment 1 for transferring biological products containers, e.g. test tubes 20, according to the invention comprises a frame 2 to which a fixed stroke pneumatic biological products container holding device 3 is connected, which slides vertically in respect of frame 2 along a vertical guiding bar 4. First shock absorbers means, comprising springs 5a and 5b on the upper and lower extremities of the frame 2, are present.

The holding device 3 comprises holding fingers 6 suitable to hold a test tube 20 and transfer it from an interfacing support 30 to a transport device 40 of biological products containers or vice-versa.

The interfacing support 30 advantageously rests on an analysis module 32 of the contents of the test tube 20, and the test tubes 20 are accommodated in the support 30 by means of test tube container 31. The configuration referred to a known system, illustrated in FIG. 6, shows the feet 33 and 34 at the base of the analysis module 32, the use of which is necessary in combination with known equipment 100.

The transport device 40 is positioned on a motorized conveyor belt 50 inserted in an automation system 60, aimed at identifying, transporting and automatically routing biological material samples. The automation system 60 rests in turn on a supporting bench 70.

Figure 3:
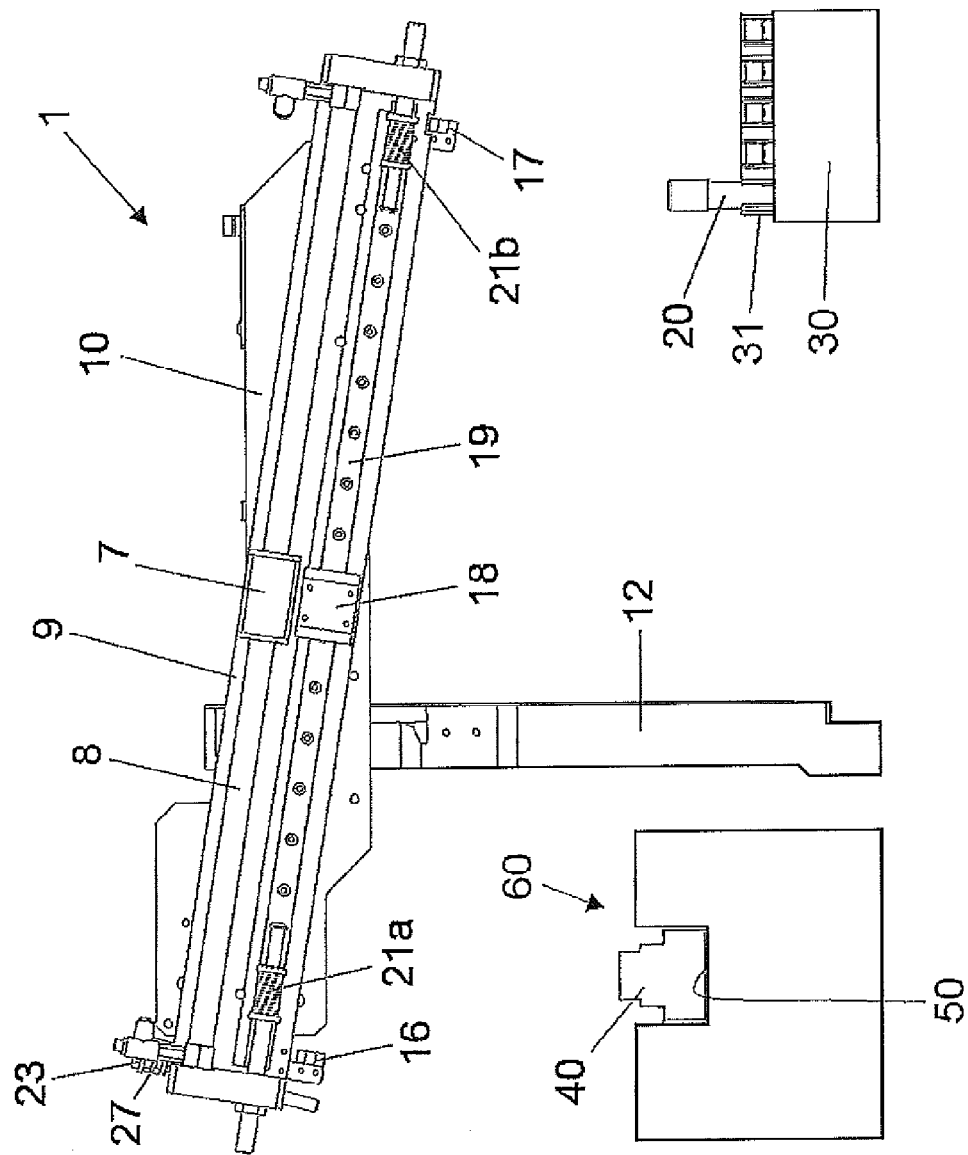
FIG. 3 is a front view of the equipment according to the invention having removed the frame and the holding device of the biological products containers.
Figure 5:
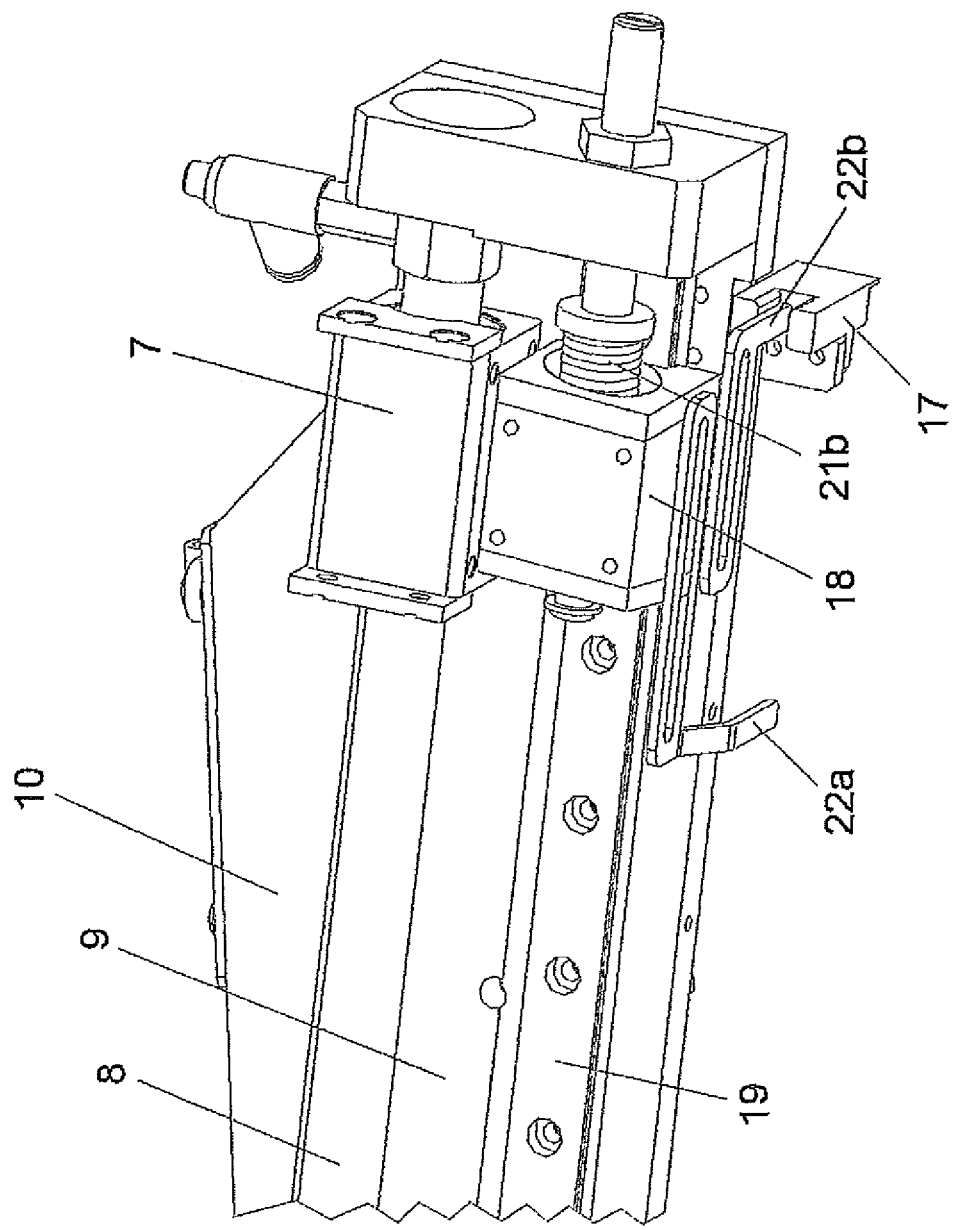
FIG. 5 shows an enlarged detail of an extremity of the inclinable body again having removed the frame and the holding device of the biological products containers.

On the wall opposite to that on which the holding device 3 is accommodated, frame 2 is connected to magnetic coupling sliding means (FIG. 3) comprising a first block 7 having a circular cavity therein (FIG. 5) so as to be able to slide along a bar 8, vertically inclined with respect to a vertical reference surface 11 and fixed at its extremities to an inclinable body 9 so that the inclination with respect to surface 11 of such inclinable body 9 is the same as the bar 8.

Furthermore, is present a second block 18 connected, and consequently also integer, to the frame 2 underneath the first block 7. Such a second block 18, in turn, is slidable along a rail 19 positioned in the lower part of the inclinable body 9, and the sliding of such a second block 18 is damped by second shock absorbing means, entirely similar to the first shock absorber means 5a and 5b, thus also comprising springs 21a and 21b arranged at the longitudinal extremities of the inclinable body 9.

End of stroke sensors 16 and 17 are further present, again in proximity of the longitudinal extremities of the inclinable body 9, but positioned on the lower edge thereof (FIG. 5), for detecting the reaching of the upper or lower sliding end of stroke point by the frame 2 by means of two appendices 22a and 22b positioned on the lower wall of the second block 18.

Figure 4:
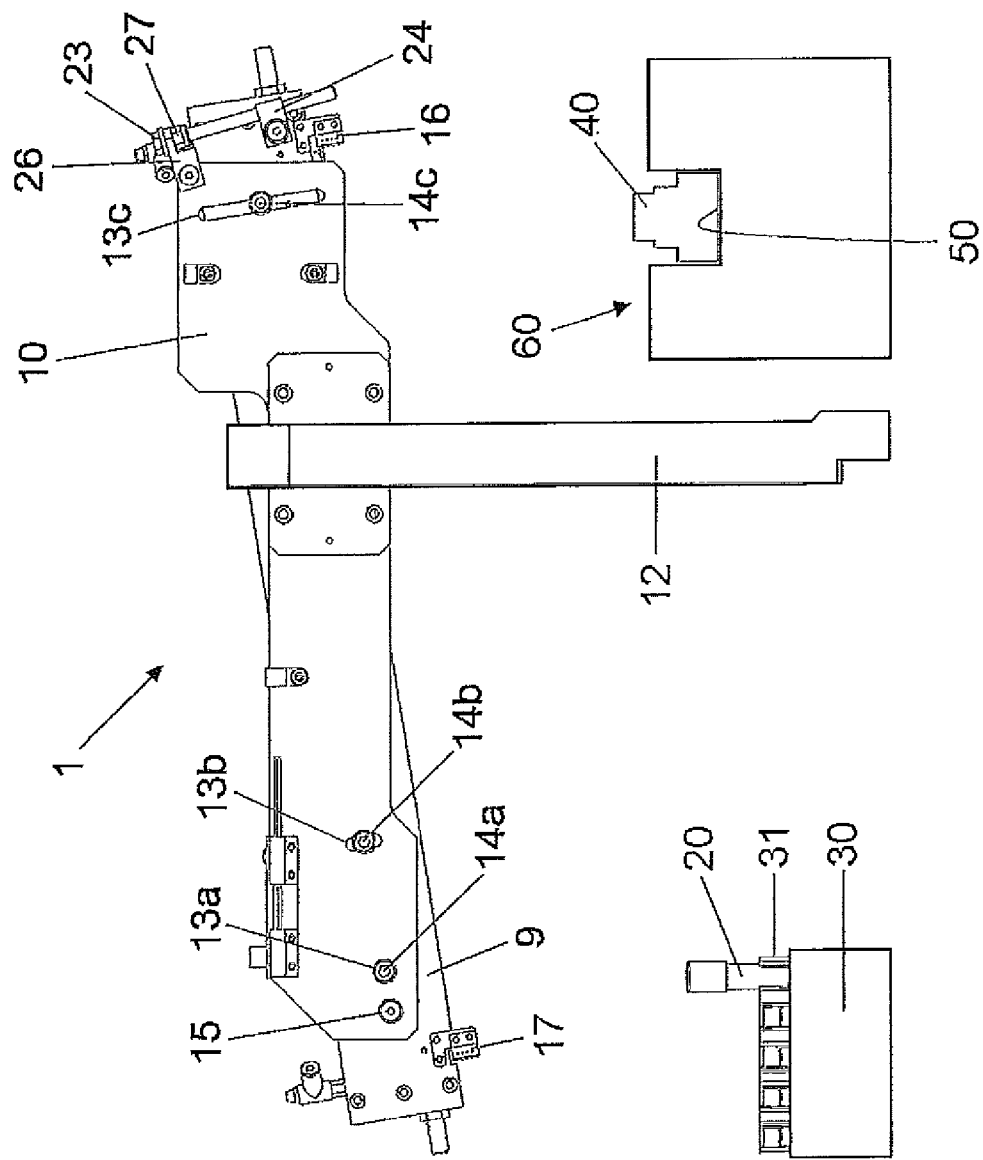
FIG. 4 is a rear view of the equipment according to the invention having removed the frame and the holding device of the biological products containers.

On the side opposite to that where the blocks 7 and 18 and frame 2 are accommodated, the inclinable body 9 is coupled to a supporting body 10 which, unlike the inclinable body 9, is not inclined with respect to the horizontal reference surface 11. Such a coupling is obtained by means of a rotation pin 15 which provides a non threaded portion in proximity of the head and a threaded portion which is screwed onto the inclinable body 9, as well as fastening screws 14a, 14b, 14c, which are screwed onto the inclinable body 9 being engaged in slots 13a, 13b, 13c obtained on the supporting body 10 (FIG. 4), slot 13c being much longer because farther away from pin 15. Pin 15 allows the reciprocal rotation between body 10 and body 9 essentially working as rotation fulcrum.

Regulation means for the inclination of the inclinable body 9 with respect to the supporting body 10 are further present comprising a regulation screw 23, which slides inside connection means to the inclinable body 9 comprising a guide 24 rotatingly associated to body 9 with rotation axis parallel to the rotation axis of body 9 coinciding with pin 15. Furthermore, the regulation screw 23, with the combined action of a tightening nut 27, is fastened on coupling means to the supporting body 10 comprising an element 26 rotatingly coupled to body 10.

A supporting upright 12 of the entire equipment 1 is perpendicularly fixed to the supporting body 10 and ideally sections the horizontal reference surface 11.

Operation is as follows: we will assume needing to move a test tube 20 from the test tube container 31 located at the interfacing support 30 to the transport device 40 positioned on the conveyor belt 50. In the illustrated embodiment, in particular FIGS. 3, 4 and 7, the height of the interfacing support 30 is lower than that of the transport device 40; in all cases, the object of the invention is reached also in the opposite case. Furthermore, as previously specified, the operation is entirely similar also in the transfer of the test tube 20 in the opposite sense, from the transport device 40 to the test tube container 31.

Furthermore, in the aforesaid embodiment the movement of equipment 1 along the direction parallel to the motorized conveyor belt 50 is not shown, is substantially the same as that of known equipment and with respect to the illustrated embodiment only contemplates a different supporting system of equipment 1 which allows the movement of the equipment itself along such a direction parallel to the conveyor belt 50.

Frame 2 is initially in rest position at the upper extremity of the inclinable body 9 and, once an appropriate command which starts movement is received from the automated laboratory, the frame is driven under the bias of magnetic coupling sliding means 7 and 18, in manner integer thereto, towards the lower extremity of the inclinable body 9 along the direction of the inclined bar 8. Also the second block 18, being connected to the frame 2, is moved jointly to the same and the first block 7, sliding along rail 19.

Such a movement is calibrated to appropriately stop when the sliding means 7, 18 reach the lower end of stroke point thereof in proximity of the lower extremity of the inclined bar 8. In this configuration, spring 21b damps the longitudinal movement of the second block 18 along rail 19 and appendix 22b, positioned under the second block 18, engages the sensor 17 positioned in proximity of the lower extremity, in longitudinal sense, of the inclinable body 9, so that reaching the lower sliding end of stroke point by the frame 2 is appropriately detected.

Figure 2:
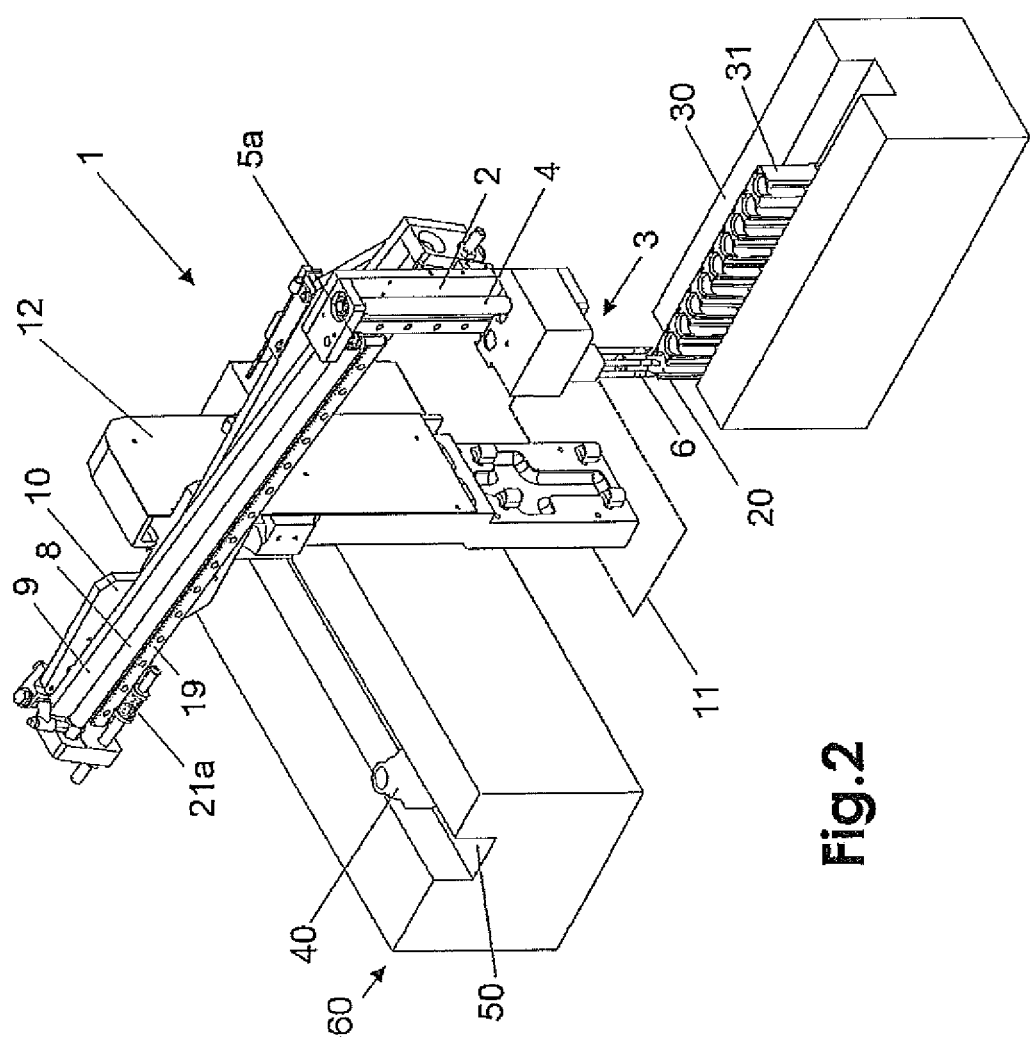
FIG. 2 is a perspective view of the equipment according to the invention with the holding device in operation.

At this point (FIG. 2), the holding device 3, which moved integrally with the frame 2 remaining in raised position, pneumatically moves down along the vertical guide bar 4 and takes the test tube 20 from the container 31 by means of fingers 6. The vertical movement of the holding device 3 is also damped by means of spring 5b.

Subsequently, the holding device 3 moves back up, being damped in its upward movement by spring 5a, withholding the test tube 20 between the fingers 6, and, again under the bias of the sliding means 7, the frame 2 moves up in opposite direction, integrally with the sliding means 7 themselves and with the second block 18, along the direction of the inclined bar 8. Such a movement is, again, calibrated to appropriately stop when frame 2 reaches the position from which it started, i.e. at the reaching by the sliding means 7, 18 of the upper end of stroke point thereof, in proximity of the upper extremity of the inclined bar 8. In entirely similar manner, the appendix 22a engages sensor 16, positioned in proximity of the upper extremity, in longitudinal sense, of the inclinable body 9; the reaching of the upper sliding end of stroke point by the frame 2 is thus determined, while the spring 21a damps the longitudinal movement along rail 19 of the second block 18.

Thus, frame 2 is exactly on the perpendicular of the transport device 40 positioned on the motorized conveyor belt 50. The holding device 3 moves down vertically unloading the test tube 20 within the transport device 40, to then move up along the vertical guide bar 4 so that equipment 1 assumes a stand-by configuration of the next test tube to be picked: the procedure is indeed repeated whenever a test tube must be transferred from the interfacing support 30 to the transport device 40, or vice-versa, in accordance with the completely automated management of the transfer of test tubes within the laboratory.

The innovative aspect of the invention is thus the handling of the frame 2 along an axis represented by the bar 8, which is not parallel to the original reference surface 11 as equipment 100 in FIG. 6, but which is inclined vertically instead. This allows to pick and release the test tube 20 at two different heights, i.e. that of the interfacing support 30 and that of the transport device 40, while maintaining the stroke vertical movement of the holding device 3 fixed.

Furthermore, the inclination of such an axis, i.e. of the bar 8 as well as of the inclinable body 9, can be accurately regulated according to such difference of height; this allows to use equipment 1 for interfacing to one another the interfacing supports 30, i.e. more in general the analysis modules 32, of variable height with respect to the ground and transport devices 40, i.e. more in general the automation systems 60, resting on the supporting benches 70, them also at variable height with respect to the ground. All this without in any case devising mechanical contrivances, e.g. the application of feet 33 and 34 to the base of the supporting bench 70 or, as in the example in FIG. 6, of the analysis module 32, to equalize the height with respect to the ground.

The inclination of the inclinable body 9 is appropriated regulated by loosening the tightening nut 27 and actuating the regulation screw 23.

In particular, the inclinable body 9 and the supporting body 10 are hinged to one another by means of pin 15 and thus, by actuating screw 23, body 9 turns with respect to the body 10 thus varying the inclination of the bar 8. Indeed, by means of a suitable tool, e.g. an adjustable wrench, the regulation screw 23 is appropriately either screwed or loosened, and such an operation contributes to varying the relative position between guide 24 connected to the inclinable body 9, and in which screw 23 slides, and element 26 connected to the supporting body 10 and fastened by the screw 23 and by the nut 27.

A screwing of the regulation screw 23 moves guide 24 towards element 26 increasing the relative inclination between inclinable body 9 and supporting body 10. Conversely, a loosening of the regulation screw 23 moves guide 24 away from element 26 decreasing the relative inclination between inclinable body 9 and supporting body 10.

Once the required inclination is reached, the inclinable body 9 and the supporting body 10 are fixed in three different points by screwing the three fastening screws 14a, 14b and 14c on the inclinable body 9.

Such fastening screws 14a, 14b and 14c may take a different position within the respective slots 13a, 13b and 13c that they engage according to the inclination between inclinable body 9 and supporting body 10 previously set by means of the regulation screw 23. In essence, the presence of the slots 13a, 13b and 13c on the supporting body 10 fixes, jointly with the length of the regulation screw 23, the relative inclination limits reachable between inclinable body 9 and supporting body 10.

In practice, it has been found that the equipment thus described can reach the set objects allowing the transfer of biological products within a diagnostics and research laboratory, from one point to another positioned at a different height and vice-versa, being in particular such two points referred to different machines between which such containers must be transferred, in accordance with the completely automated management of the containers within the laboratory.

The equipment can be regulated according to the possible different heights with respect to the surface of the machines between which the biological products containers must be transferred, i.e. according to the difference of height existing between the two machines. This allows to avoid the use of any type of mechanical contrivance aimed at equalizing the heights of the two machines, e.g. the application of feet to the lower of the twos raising the height thereof with respect to the ground, as instead occurred in the known equipment.

Furthermore, the device which is used to hold, transfer and release the biological products containers from one point to another is very reliable, preventing the containers from being incorrectly released at the arrival point, e.g. because they were held either too far up or too far down in the interfacing point, or even from being dropped during transfer.

The invention thus described is susceptible to many changes and variants, all comprised within the scope of the inventive concept.

In practice, the materials used as well as the shapes and size may be any, according to needs.

The invention claimed is:

1. Equipment for transferring biological products containers from a horizontal interface support to a horizontal transport device and vice-versa for biological containers, positioned at different heights, comprising
    a frame to which a holding device for biological products containers is connected vertically mobile in respect of said frame and provided with fingers suitable to hold, transfer and release a container for biological products,
    a vertical column supporting a horizontal sustaining body,
    an inclinable body rotatably connected to said horizontal sustaining body,
    regulation means for the inclination of said inclinable body,
    said frame being integer with sliding means along a bar fixed to the inclinable body,
    said regulation means including a regulation screw coupled to a first coupling means rotatably associated to said inclinable body and to a second coupling means rotatably associated to said sustaining body, said coupling means providing rotation axes parallel between them and parallel to the axis of rotation of the inclinable body in respect of the sustaining body, said regulation screw providing an axis of rotation orthogonal to said axes of rotation of the coupling means, said coupling means moving reciprocally in function of the direction of rotation of the regulation screw,
    said holding device being a fixed stroke vertically mobile device,
    said vertical column being positioned between said horizontal interface support and said horizontal transport device,
    said horizontal sustaining body being fixed to said vertical column far from the lateral ends of the horizontal sustaining body in order to allow the positioning of said horizontal interface support and said horizontal transport device under said lateral ends of the horizontal sustaining body.

2. The equipment according to claim 1, wherein the inclinable body is hinged to said sustaining body by a rotation pin.

3. The equipment according to claim 2 wherein said sliding means include a first block slidable along a first rail and a second block slidable along a second rail, said rails are parallel between them, said blocks are integer among them, the first block supporting the frame and the second block interacting with shock absorbers.

4. The equipment according to claim 3, wherein to said inclinable body, in proximity of its extremities, end of stroke sensors are connected with which appendices of the sliding means of the frame interact.

5. The equipment according to claim 1, wherein said sliding means include a first block slidable along a first rail and a second block slidable along a second rail, said rails are parallel between them, said blocks are integer among them, the first block supporting the frame and the second block interacting with shock absorbers.

\* \* \* \* \*